(12) United States Patent
Rowe

(10) Patent No.: US 11,965,418 B2
(45) Date of Patent: Apr. 23, 2024

(54) DOWNHOLE OPTICAL EMISSION SPECTROSCOPY

(71) Applicant: Halliburton Energy Services, Inc., Houston, TX (US)

(72) Inventor: Mathew Dennis Rowe, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 219 days.

(21) Appl. No.: 17/550,556

(22) Filed: Dec. 14, 2021

(65) Prior Publication Data
US 2023/0184106 A1 Jun. 15, 2023

(51) Int. Cl.
| | |
|---|---|
| *G01J 3/02* | (2006.01) |
| *E21B 49/00* | (2006.01) |
| *G01J 3/443* | (2006.01) |
| *G01N 21/03* | (2006.01) |
| *G01N 21/67* | (2006.01) |

(52) U.S. Cl.
CPC ............ *E21B 49/003* (2013.01); *E21B 49/00* (2013.01); *G01J 3/0205* (2013.01); *G01J 3/027* (2013.01); *G01J 3/443* (2013.01); *G01N 21/0303* (2013.01); *G01N 21/67* (2013.01)

(58) Field of Classification Search
CPC ........ E21B 49/003; E21B 49/00; E21B 47/12; E21B 47/26; G01J 3/0205; G01J 3/027; G01J 3/443; G01J 2003/2833; G01J 2003/284; G01N 21/0303; G01N 21/67
See application file for complete search history.

(56) References Cited

U.S. PATENT DOCUMENTS

| | | | | |
|---|---|---|---|---|
| 6,227,293 | B1* | 5/2001 | Huffman | E21B 43/003 166/177.2 |
| 8,613,312 | B2* | 12/2013 | Zolezzi-Garreton | E21B 43/003 166/177.2 |
| 11,078,727 | B2 | 8/2021 | Gleitman et al. | |
| 2006/0102343 | A1 | 5/2006 | Skinner et al. | |
| 2016/0010440 | A1 | 1/2016 | Sizonenko et al. | |
| 2016/0244349 | A1* | 8/2016 | St. John | C02F 9/00 |
| 2019/0177210 | A1* | 6/2019 | Beall | A61K 6/824 |
| 2019/0345060 | A1* | 11/2019 | Chen | C04B 33/34 |

(Continued)

FOREIGN PATENT DOCUMENTS

WO 2014197646 A1 12/2014

OTHER PUBLICATIONS

International Search Report and Written Opinion, PCT/US2021/063698, dated Sep. 7, 2022, 10 pages.

*Primary Examiner* — Abdullahi Nur
(74) *Attorney, Agent, or Firm* — Kilpatrick Townsend & Stockton LLP

(57) ABSTRACT

A system includes a discharge tool positioned within a wellbore and configured to generate an electrical discharge that interacts with a rock formation proximate to the discharge tool, wherein the interaction of the electrical discharge with the rock formation vaporizes a portion of the rock formation to generate a discharge plasma. The system further includes an optical emission spectroscopy (OES) sub-system configured to determine an elemental composition of the portion of the rock formation based on optical emission generated by the discharge plasma, wherein at least a portion of the OES sub-system is positioned within the wellbore.

18 Claims, 5 Drawing Sheets

(56) References Cited

U.S. PATENT DOCUMENTS

2020/0370375 A1* 11/2020 Gleitman .................. E21B 7/15
2021/0310309 A1* 10/2021 Kronman .................. E21B 7/15

* cited by examiner

DOWNHOLE OPTICAL EMISSION SPECTROSCOPY

TECHNICAL FIELD

The present disclosure relates generally to well logging operations and, more particularly, to downhole optical emission spectroscopy.

BACKGROUND

Modern oil field operators demand access to a great quantity of information regarding the parameters and conditions encountered downhole. Such information typically includes characteristics of the earth formations traversed by the wellbore and data relating to the size and configuration of the wellbore itself. The collection of information relating to conditions downhole, which commonly is referred to as "logging," can be performed by several methods including wireline logging and "logging while drilling" (LWD).

In wireline logging, a probe or "sonde" is lowered into the wellbore after some or all of the well has been drilled. The sonde hangs at the end of a long cable or "wireline" that provides mechanical support to the sonde and also provides an electrical connection between the sonde and electrical equipment located at the surface of the well. In accordance with existing logging techniques, various parameters of the earth's formations are measured and correlated with the position of the sonde in the wellbore as the sonde is pulled uphole.

In LWD, the drilling assembly includes sensing instruments that measure various parameters as the formation is being penetrated, thereby enabling measurements of the formation while it is less affected by fluid invasion. While LWD measurements are desirable, drilling operations create an environment that is generally hostile to electronic instrumentation, telemetry, and sensor operations.

Traditional logging methods are unable to perform accurate elemental composition analysis of a rock formation proximate to a wellbore.

BRIEF DESCRIPTION OF DRAWINGS

Some specific exemplary aspects of the disclosure may be understood by referring, in part, to the following description and the accompanying drawings.

Figure 1:
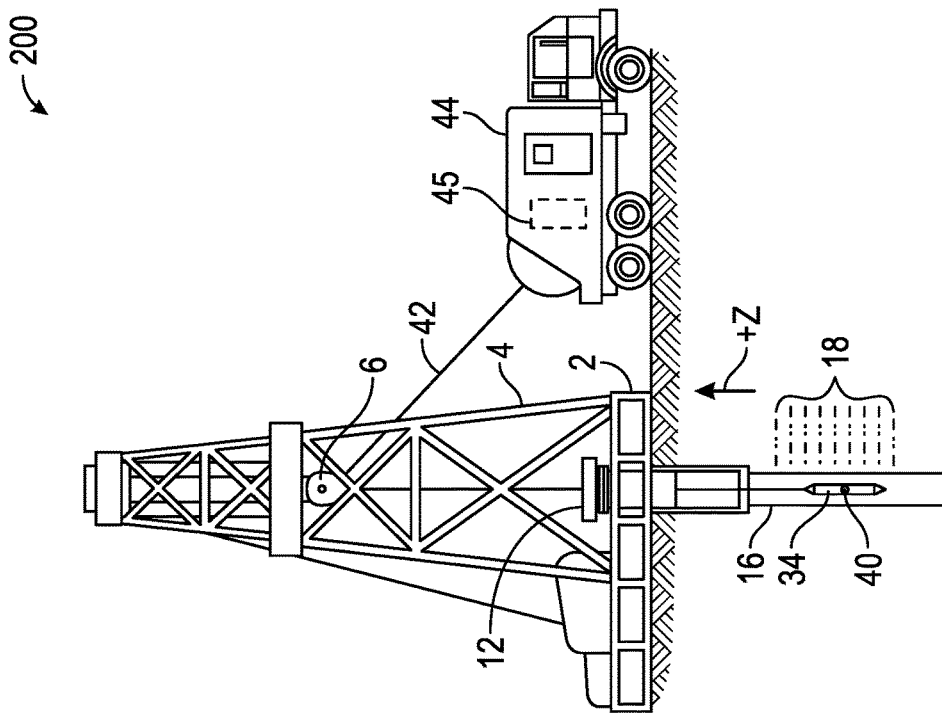
FIG. 1 shows an illustrative logging while drilling (LWD) system, in accordance with one or more aspects of the present disclosure.

While aspects of this disclosure have been depicted and described and are defined by reference to exemplary aspects of the disclosure, such references do not imply a limitation on the disclosure, and no such limitation is to be inferred. The subject matter disclosed is capable of considerable modification, alteration, and equivalents in form and function, as will occur to those skilled in the pertinent art having the benefit of this disclosure. The depicted and described aspects of this disclosure are examples only, and not exhaustive of the scope of the disclosure.

DETAILED DESCRIPTION

The present application relates to determining elemental composition of a rock formation surrounding a wellbore. The techniques for determining the elemental composition of a rock formation surrounding a wellbore provide several advantages.

Since properties of the rock formation proximate to the wellbore being drilled plays a major role in optimizing the drilling through the rock formation, knowing the elemental composition of the rock formation may be highly beneficial in achieving better drilling optimization. For example, knowledge of the elemental composition of the rock formation may help determine the optimal well placement and drilling parameters to be used for drilling the wellbore through the formation. Present logging techniques are incapable of determining the complete elemental composition of a rock formation surrounding a wellbore.

Aspects of the present disclosure discuss systems and methods for in-place and real time elemental composition analysis of rock formations proximate to a wellbore using Optical Emission Spectroscopy (OES). As described in more detail below, an OES system discussed in accordance with one or more embodiments of this disclosure includes a discharge tool that can be positioned within the wellbore near a region of interest of the rock formation. The discharge tool is designed to generate an electrical discharge that interacts with a portion of the rock formation surrounding the wellbore to produce a discharge plasma. The OES system further includes an OES sub-system designed to analyze an optical emission generated by the discharge plasma to determine an elemental composition of the portion of the rock formation.

As further described in this disclosure, the term "in-place" refers to OES analysis of the rock formation at location within the wellbore, for example, without transporting portions of the rock formation to a different location (e.g., surface) for the analysis as is done by certain present techniques. By performing in-place elemental composition analysis of the rock formation surrounding the wellbore, elemental composition of the rock formation may be determined accurately at particular depths within the wellbore. In addition, real time determination of the elemental composition of the rock formation while drilling the wellbore allows real-time adjustment of operating parameters related to the drilling process to achieve a more optimal drilling of the wellbore.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components. It may also include one or more interface units capable of transmitting one or more signals to a controller, actuator, or like device.

For the purposes of this disclosure, computer-readable media may include any instrumentality or aggregation of instrumentalities that may retain data and/or instructions for a period of time. Computer-readable media may include, for example, without limitation, storage media such as a direct access storage device (for example, a hard disk drive or floppy disk drive), a sequential access storage device (for example, a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Illustrative aspects of the present disclosure are described in detail herein. In the interest of clarity, not all features of an actual implementation may be described in this specification. It will of course be appreciated that in the development of any such actual aspect, numerous implementation-specific decisions are made to achieve the specific implementation goals, which will vary from one implementation to another. Moreover, it will be appreciated that such a development effort might be complex and time-consuming, but would, nevertheless, be a routine undertaking for those of ordinary skill in the art having the benefit of the present disclosure.

To facilitate a better understanding of the present disclosure, the following examples of certain aspects are given. In no way should the following examples be read to limit, or define, the scope of the invention. Aspects of the present disclosure may be applicable to horizontal, vertical, deviated, or otherwise nonlinear wellbores in any type of subterranean formation. Aspects may be applicable to injection wells as well as production wells, including hydrocarbon wells. Aspects may be implemented using a tool that is made suitable for testing, retrieval and sampling along sections of the formation. Aspects may be implemented with tools that, for example, may be conveyed through a flow passage in tubular string or using a wireline, slickline, coiled tubing, downhole robot or the like. "Measurement-while-drilling" ("MWD") is the term generally used for measuring conditions downhole concerning the movement and location of the drilling assembly while the drilling continues. "Logging-while-drilling" ("LWD") is the term generally used for similar techniques that concentrate more on formation parameter measurement. Devices and methods in accordance with certain aspects may be used in one or more of wireline (including wireline, slickline, and coiled tubing), downhole robot, MWD, and LWD operations.

FIG. 1 shows an illustrative logging while drilling (LWD) system 100 in which aspects of the present disclosure may be practiced. A drilling platform 2 supports a derrick 4 having a traveling block 6 for raising and lowering a drill string 8. A kelly 10 supports the drill string 8 as it is lowered through a rotary table 12. A drill bit 14 is driven by a downhole motor and/or rotation of the drill string 8. As the drill bit 14 rotates, it creates a wellbore 16 that passes through various formations 18. A pump 20 circulates drilling fluid through a feed pipe 22 to the kelly 10, downhole through the interior of drill string 8, through orifices in drill bit 14, back to the surface via the annulus around drill string 8, and into a retention pit 24. The drilling fluid transports cuttings from the wellbore 16 into the pit 24 and aids in maintaining the wellbore integrity.

An LWD tool 26 may be integrated into a bottom-hole assembly (BHA) 32 near the drill bit 14. As the drill bit 14 extends the wellbore 16 through the formations, the logging tool 26 collects measurements relating to various formation properties as well as the tool orientation and various other drilling conditions. The logging tool 26 may take the form of a drill collar, for example, a thick-walled tubular that provides weight and rigidity to aid the drilling process. A telemetry sub 28 may be included to transfer tool measurements to a surface receiver 30 and to receive commands from the surface. In one or more aspects, the telemetry sub 28 does not communicate with the surface, but rather stores logging data for later retrieval at the surface when the logging assembly is recovered. In both approaches, limitations may be placed on the amount of data that can be collected and stored or communicated to the surface. In certain aspects, the LWD system 100 includes a data processing system 50 (for example, a computer system) positioned at the surface. The data processing system 50 may be communicably coupled to the surface receiver 30 and may receive data collected by the logging tool 26 and/or transmit commands to the logging tool 26 through the surface receiver 30. The data processing system 50 may process the data and generate visualizations for display so as to aid a human operator in steering the wellbore with respect to bed boundaries and/or other wellbores, for example, towards hydrocarbon deposits. In one embodiment, as will be described below, the data processing system 50 may process optical emission data collected by the logging tool 26 and determine an elemental composition of the rock formation 18 proximate to the wellbore 16. The determined elemental composition of the rock formation 18 may be used to adjust one or more drilling parameters.

In one or more embodiments, pulsed-power drilling may be employed to drill wellbore 16. Pulsed-power drilling uses pulsed power technology to drill a wellbore (e.g., wellbore 16) in a rock formation (e.g., rock formation 18). Pulsed-power technology includes repeatedly applying a high electric potential across electrodes of a pulsed-power drill bit, which ultimately causes the surrounding rock to fracture. The fractured rock is carried away from the bit by drilling fluid and the bit advances downhole. For example, for a pulse-power drilling operation, the drill bit 14 may be a pulsed-power drill bit. Power may be supplied to the drill bit 14 from components downhole, components at the surface and/or a combination of components downhole and at the surface. For example, a generator (not expressly shown in FIG. 1) may generate electrical power at the surface. The generated electrical energy may be transmitted downhole via a surface cable and a sub-surface cable (not expressly shown in FIG. 1) contained within drill string 8 or attached to the outer wall of the drill string 8. A pulse-generating (PG) circuit within BHA 32 may receive the electrical energy from the generator and may generate high-energy electrical pulses to drive drill bit 14.

The PG circuit within BHA 32 may be utilized to repeatedly apply a large electric potential across the electrodes of drill bit 14. Each application of electric potential is referred to as a pulse. The high-energy electrical pulses generated by the PG circuit may be referred to as pulse drilling signals. When the electric potential across the electrodes of drill bit 14 is increased during a pulse to generate a sufficiently high electric field, an electrical discharge (e.g., electrical arc or spark) forms through rock formation 18 at the distal end of wellbore 16. The discharge temporarily forms an electrical coupling between the electrodes of drill bit 14, allowing electric current to flow through the discharge inside a portion of the rock formation 18 at the distal end of wellbore 16. The discharge greatly increases the temperature and pressure of the portion of the rock formation 18 through which the discharge flows and the surrounding formation and materials. The temperature and pressure are sufficiently high to break the rock into small bits referred to as cuttings. This fractured rock is removed, typically by drilling fluid 22, which moves the fractured rock away from the electrodes and uphole.

Figure 2:
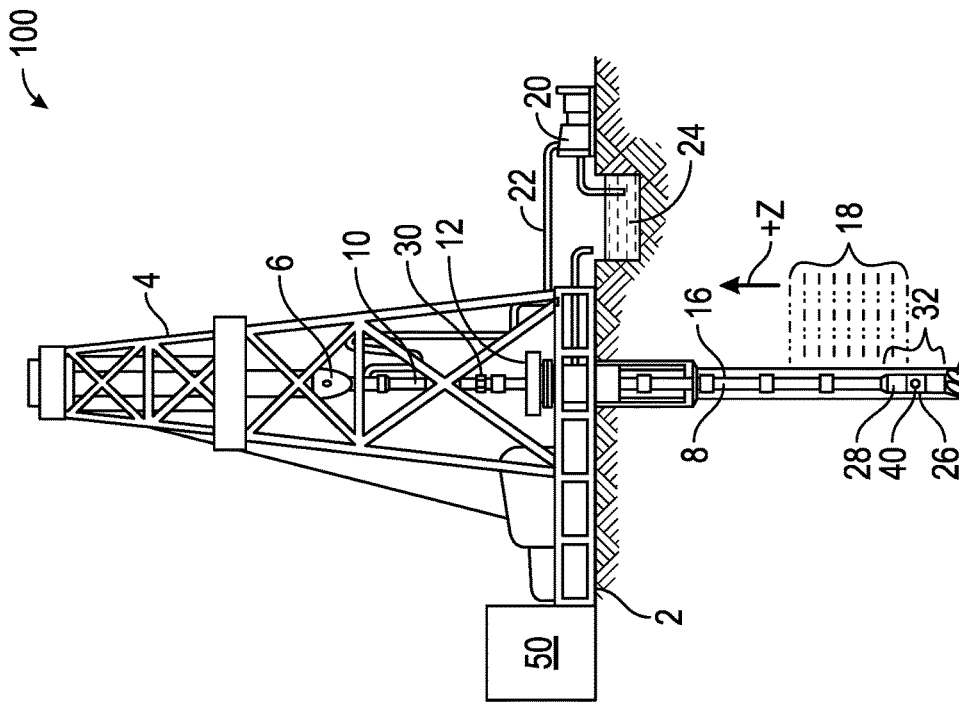
FIG. 2 shows an illustrative wireline logging system, in accordance with one or more aspects of the present disclosure.

At various times during the drilling process, the drill string 8 may be removed from the wellbore as shown in the wireline logging system 200 of FIG. 2. Once the drill string has been removed, logging operations can be conducted using a wireline logging tool 34, for example, a sensing instrument sonde suspended by a cable 42 having conductors for transporting power to the tool and telemetry from the tool to the surface. A wireline logging tool 34 may have pads, centralizing springs or both to maintain the logging tool 34 near the axis of the wellbore 16 as the logging tool 34 is pulled uphole. A logging facility 44 collects measurements from the logging tool 34 and includes a data processing system 45 (for example, computer system) for storing and processing the measurements gathered by the logging tool 34. As will be described below, the data processing system 45 may process optical emission data collected by the logging tool 34 and determine an elemental composition of the rock formation 18 proximate to the wellbore 16. The determined elemental composition of the rock formation 18 may be used to adjust one or more drilling parameters.

In each of the foregoing logging environments, the logging tools 26 and 34 of the LWD system of FIG. 1 and the wireline logging system of FIG. 2 respectively preferably include a navigational sensor package 40 that includes directional sensors for determining the inclination angle, the horizontal angle, and the rotational angle (a.k.a. "tool face angle") of the BHA. As is commonly defined in the art, the inclination angle is the deviation from vertically downward, the horizontal angle is the angle in a horizontal plane from true North, and the tool face angle is the orientation (rotational about the tool axis) angle from the high side of the wellbore. In accordance with known techniques, wellbore directional measurements can be made as follows: a three-axis accelerometer measures the earth's gravitational field vector relative to the tool axis and a point on the circumference of the tool called the "tool face scribe line". The tool face scribe line is typically drawn on the surface of the logging tool 26 or logging tool 34 as a line parallel to the tool axis. From this measurement, the inclination and tool face angle of the BHA can be determined. Additionally, a three-axis magnetometer measures the earth's magnetic field vector in a similar manner. From the combined magnetometer and accelerometer data, the horizontal angle of the BHA may be determined.

Moreover, the logging tool in each of the foregoing environments may measure at least one formation parameter as a function of tool depth (or position along the wellbore), azimuth, and radial distance from the wellbore axis. Such measurements may be made, for example, by a downhole optical emission spectrometer. Other suitable logging tools may include an azimuthally sensitive resistivity logging tool having multiple depths of investigation, a "wellbore radar" assembly that detects reflections of high-frequency electromagnetic waves, or ultrasonic imaging tools that similarly detect reflections of acoustic impulses. Certain nuclear logging tools may also provide formation property measurements as a function of position, azimuth, and radial distance. Of course, data from multiple tools can also be combined to further characterize formation properties.

As such logging tools progress along the wellbore, they rotate, employ an azimuthally-distributed array and/or direct azimuthally-steerable sensors 40 to collect measurements as a function of azimuth and radial distance. In some aspects, (for example, wireline logging sondes that do not move too quickly), all of the logging data can be conveyed to the surface as it is collected. Such information can be quite valuable to enable the driller to steer the wellbore with respect to bed boundaries and/or other wellbores, thereby, for example, increasing path lengths through the payzone.

Figure 3:
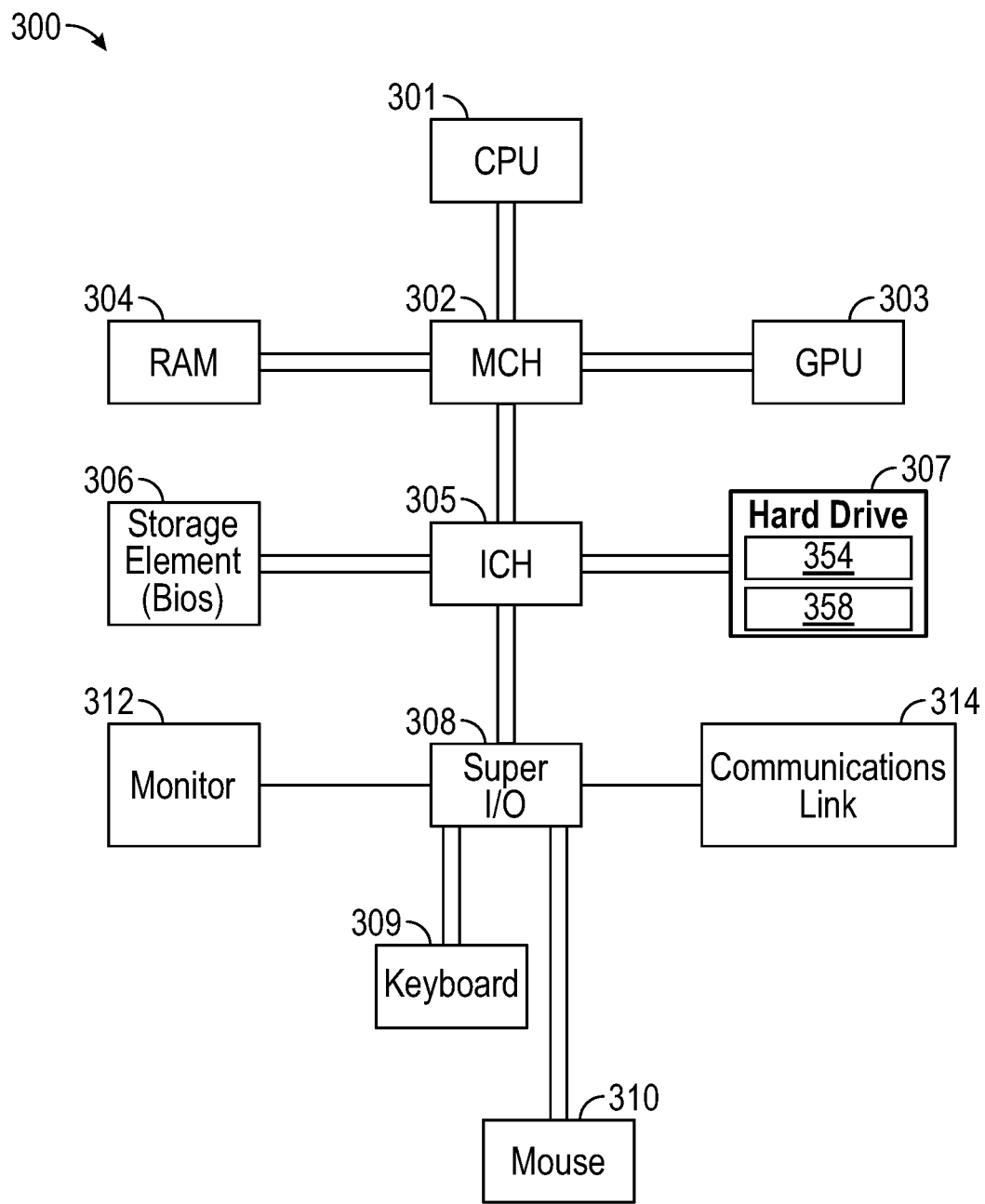
FIG. 3 is a diagram illustrating an example information handling system, in accordance with one or more aspects of the present disclosure.

FIG. 3 is a diagram illustrating an example information handling system 300, for example, for use with or by the LWD system of FIG. 1 or the wireline logging system of FIG. 2, according to one or more aspects of the present disclosure. The data processing systems 45 and 50 discussed above with reference to FIGS. 1 and 2 may take a form similar to the information handling system 300. A processor or central processing unit (CPU) 301 of the information handling system 300 is communicatively coupled to a memory controller hub (MCH) or north bridge 302. The processor 301 may include, for example a microprocessor, microcontroller, digital signal processor (DSP), application specific integrated circuit (ASIC), or any other digital or analog circuitry configured to interpret and/or execute program instructions and/or process data. Processor 301 may be configured to interpret and/or execute program instructions or other data retrieved and stored in any memory such as memory 304 or hard drive 307. Program instructions or other data may constitute portions of a software or application, for example application 358 or data 354, for carrying out one or more methods described herein. Memory 304 may include read-only memory (ROM), random access memory (RAM), solid state memory, or disk-based memory. Each memory module may include any system, device or apparatus configured to retain program instructions and/or data for a period of time (for example, non-transitory computer-readable media). For example, instructions from a software or application 358 or data 354 may be retrieved and stored in memory 304 for execution or use by processor 301. In one or more aspects, the memory 304 or the hard drive 307 may include or comprise one or more non-transitory executable instructions that, when executed by the processor 301 cause the processor 301 to perform or initiate one or more operations or steps. The information handling system 300 may be preprogrammed or it may be programmed (and reprogrammed) by loading a program from another source (for example, from a CD-ROM, from another computer device through a data network, or in another manner).

The data 354 may include treatment data, geological data, fracture data, seismic or micro seismic data, or any other appropriate data. In one or more aspects, a memory of a computing device includes additional or different data, application, models, or other information. In one or more aspects, the data 354 may include geological data relating to one or more geological properties of the subterranean formation (for example, formation 18 shown in FIG. 1). For example, the geological data may include information on the wellbore, completions, or information on other attributes of the subterranean formation. In one or more aspects, the geological data includes information on the lithology, fluid content, stress profile (for example, stress anisotropy, maximum and minimum horizontal stresses), pressure profile, spatial extent, or other attributes of one or more rock formations in the subterranean zone. The geological data may include information collected from well logs, rock samples, outcroppings, seismic or microseismic imaging, or other data sources.

Figure 5:
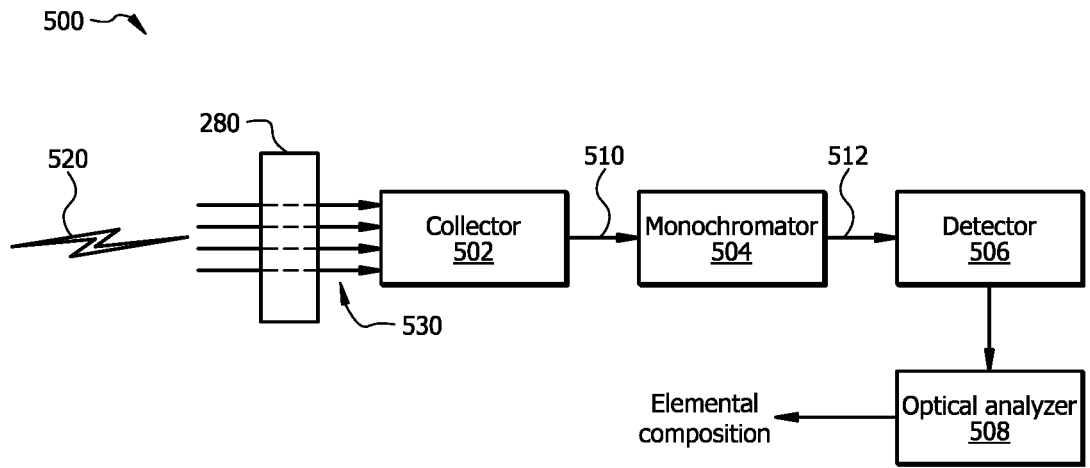
FIG. 5 illustrates an OES sub-system, in accordance with one or more embodiments of the present disclosure.
Figure 6:
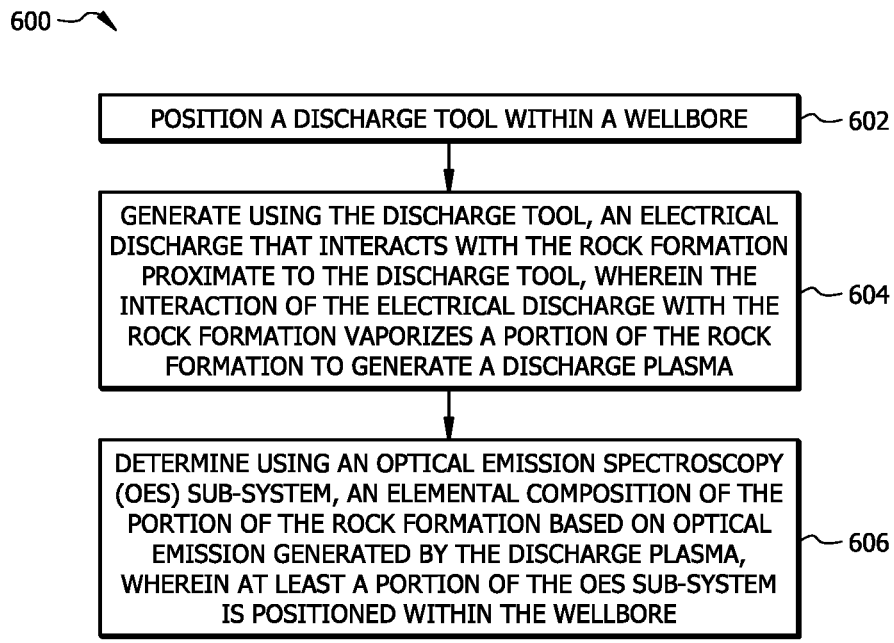
FIG. 6 illustrates example operations for determining elemental composition of a rock formation, in accordance with certain aspects of the present disclosure.

The one or more applications 358 may comprise one or more software applications, one or more scripts, one or more programs, one or more functions, one or more executables, or one or more other modules that are interpreted or executed by the processor 301. The one or more applications 358 may include one or more machine-readable instructions for performing one or more of the operations related to any one or more aspects of the present disclosure. The one or more applications 358 may include machine-readable instructions for processing and visualization of resistivity data, as illustrated in FIGS. 4-6. The one or more applications 358 may obtain input data, such as seismic data, well data, treatment data, geological data, fracture data, or other types of input data, from the memory 304, from another local source, or from one or more remote sources (for example, via the one or more communication links 314). The one or more applications 358 may generate output data and store the output data in the memory 304, hard drive 307, in another local medium, or in one or more remote devices (for example, by sending the output data via the communication link 314).

Modifications, additions, or omissions may be made to FIG. 3 without departing from the scope of the present disclosure. For example, FIG. 3 shows a particular configuration of components of information handling system 300. However, any suitable configurations of components may be used. For example, components of information handling system 300 may be implemented either as physical or logical components. Furthermore, in one or more aspects, functionality associated with components of information handling system 300 may be implemented in special purpose circuits or components. In other aspects, functionality associated with components of information handling system 300 may be implemented in configurable general purpose circuit or components. For example, components of information handling system 300 may be implemented by configured computer program instructions.

Memory controller hub 302 may include a memory controller for directing information to or from various system memory components within the information handling system 300, such as memory 304, storage element 306, and hard drive 307. The memory controller hub 302 may be coupled to memory 304 and a graphics processing unit (GPU) 303. Memory controller hub 302 may also be coupled to an I/O controller hub (ICH) or south bridge 305. I/O controller hub 305 is coupled to storage elements of the information handling system 300, including a storage element 306, which may comprise a flash ROM that includes a basic input/output system (BIOS) of the computer system. I/O controller hub 305 is also coupled to the hard drive 307 of the information handling system 300. I/O controller hub 305 may also be coupled to an I/O chip or interface, for example, a Super I/O chip 308, which is itself coupled to several of the I/O ports of the computer system, including a keyboard 309, a mouse 310, a monitor 312 and one or more communications link 314. Any one or more input/output devices receive and transmit data in analog or digital form over one or more communication links 314 such as a serial link, a wireless link (for example, infrared, radio frequency, or others), a parallel link, or another type of link. The one or more communication links 314 may comprise any type of communication channel, connector, data communication network, or other link. For example, the one or more communication links 314 may comprise a wireless or a wired network, a Local Area Network (LAN), a Wide Area Network (WAN), a private network, a public network (such as the Internet), a wireless fidelity or WiFi network, a network that includes a satellite link, or another type of data communication network.

As described above, properties of a rock formation 18 proximate to a wellbore 16 being drilled may be measured by several logging techniques. Data relating to the properties of the rock formation 18 collected using the logging techniques may be used to optimize the drilling operation. The oil filed industry is always striving to device better ways to optimize the drilling of a wellbore 16 through a given rock formation 18. Since properties of the rock formation 18 proximate to the wellbore 16 being drilled plays a major role in optimizing the drilling through the rock formation 18, knowing the elemental composition of the rock formation 18 may be highly beneficial in achieving better drilling optimization. For example, knowledge of the elemental composition of the rock formation 18 may help determine the optimal well placement and drilling parameters to be used for drilling the wellbore 16 through the formation 18. Present logging techniques are incapable of determining the complete elemental composition of a rock formation 18 surrounding a wellbore 16. Some logging techniques may help identify certain bulk elements of a rock formation such as aluminum, iron, silicon, carbonates etc. However, no present logging technique can perform a complete elemental composition analysis of the rock formation 18 and determine the constituent elements of the rock formation 18 and their corresponding concentrations in the rock formation 18. Some present methods perform limited elemental composition analysis by transporting cuttings of the rock formation 18 to the surface and then analyzing the rock cuttings on the surface to determine certain constituent elementals of the formation 18. However, this method is not ideal and presents various challenges. For example, it is hard to collect rock cuttings at particular desired depths within the wellbore 16. The rock cuttings are transported to the surface via a single channel extending from the drill bit 14 to the surface, and rock cuttings collected at different depths often get mixed up. Thus, it is hard to accurately determine elemental compositions of the rock formation 18 at particular depths. Further, such techniques do not provide real time data regarding the composition of the formation 18 while drilling is in progress. Accordingly, the limited data produced by such techniques cannot be used in real time adjustments of the drilling operation.

Aspects of the present disclosure discuss systems and methods for in-place and real time elemental composition analysis of rock formations proximate to a wellbore using Optical Emission Spectroscopy (OES). As described below, the disclosed systems and techniques leverage the pulse-power drilling technology to perform the OES of the rock formations. The term "in-place" refers to OES analysis of the rock formation at location within the wellbore, for example, without transporting portions of the rock formation to a different location (e.g., surface) for the analysis as is done by certain present techniques.

As described in more detail below, the OES system discussed in accordance with one or more embodiments of this disclosure includes a discharge tool that can be positioned within the wellbore and is designed to generate an electrical discharge that interacts with a portion of the rock formation surrounding the wellbore to produce a discharge plasma. The OES system further includes an OES subsystem designed to analyze an optical emission generated by the discharge plasma to determine an elemental composition of the portion of the rock formation. In one or more embodiments, the discharge tool may be based on the principle and design of a pulsed-power drill bit described above.

Figure 4A:
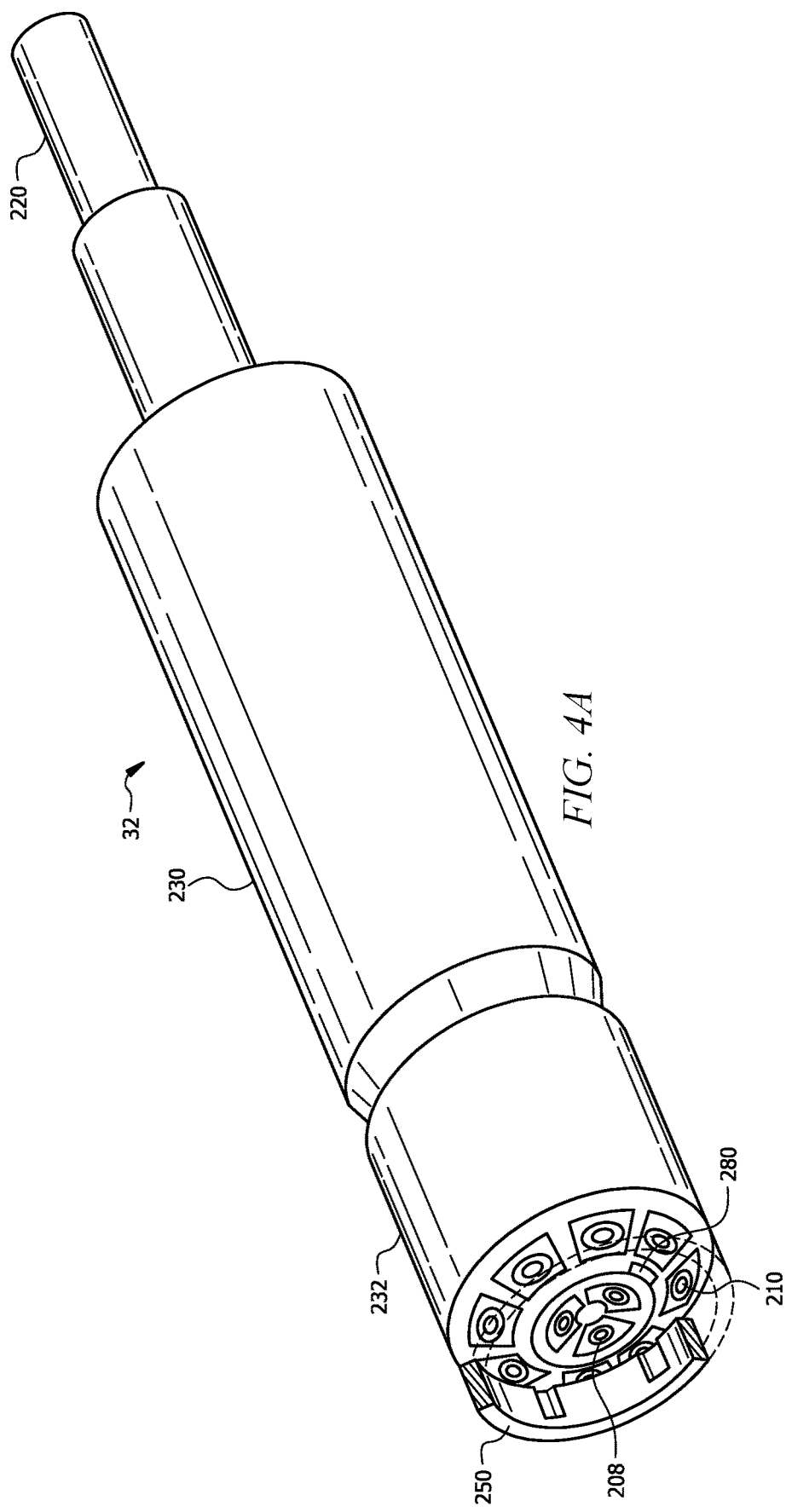
FIG. 4A is a perspective view of exemplary components of a bottom-hole assembly, in accordance with one or more embodiments of the present disclosure.

FIG. 4A is a perspective view of exemplary components of a bottom-hole assembly (e.g., BHA 32), in accordance with one or more embodiments of the present disclosure. BHA 32 may include a discharge tool 230 including a discharger 232. The discharge tool 230 leverages the pulse-power drilling technology to generate electrical discharges. For example, the discharger 232 may generate electrical discharges similar to a pulsed-power drill bit used in pulsed-power drilling. For the purposes of the present disclosure, discharger 232 may be integrated within discharge tool 230, or may be a separate component coupled to discharge tool 230.

Discharge tool 230 may provide pulsed electrical energy to discharger 232. Discharge tool 230 receives electrical power from a power source via cable 220. For example, discharge tool 230 may receive electrical power via cable 220 from a power source located on the surface or from a power source located downhole such as a generator powered by a mud turbine. Discharge tool 230 may also receive electrical power via a combination of a power source located on the surface and a power source located downhole. Discharger 232 may include one or more electrodes 208 and 210 and a ground ring 250, shown in part in FIG. 4A. Ground ring 250 may function as an electrode. Discharge tool 230 converts electrical power received from the power source into high-energy electrical pulses that are applied across electrodes 208 and/or 210 and ground ring 250 of the discharger 232. Discharge tool 230 may include a PG circuit as described above with reference to FIG. 1.

Although illustrated as a contiguous ring in FIG. 4A, ground ring 250 may be non-contiguous discrete electrodes and/or implemented in different shapes. Each of electrodes 208 and 210 may be positioned at a minimum distance from ground ring 250 of approximately 0.4 inches and at a maximum distance from ground ring 250 of approximately 6 inches. The distance between electrodes 208 or 210 and ground ring 250 may be based on the parameters of the discharge operation and/or on the diameter of discharger 232. For example, the distance between electrodes 208 or 210 and ground ring 250, at their closest spacing, may be at least 0.4 inches, at least 1 inch, at least 1.5 inches, or at least 2 inches.

Figure 4B:
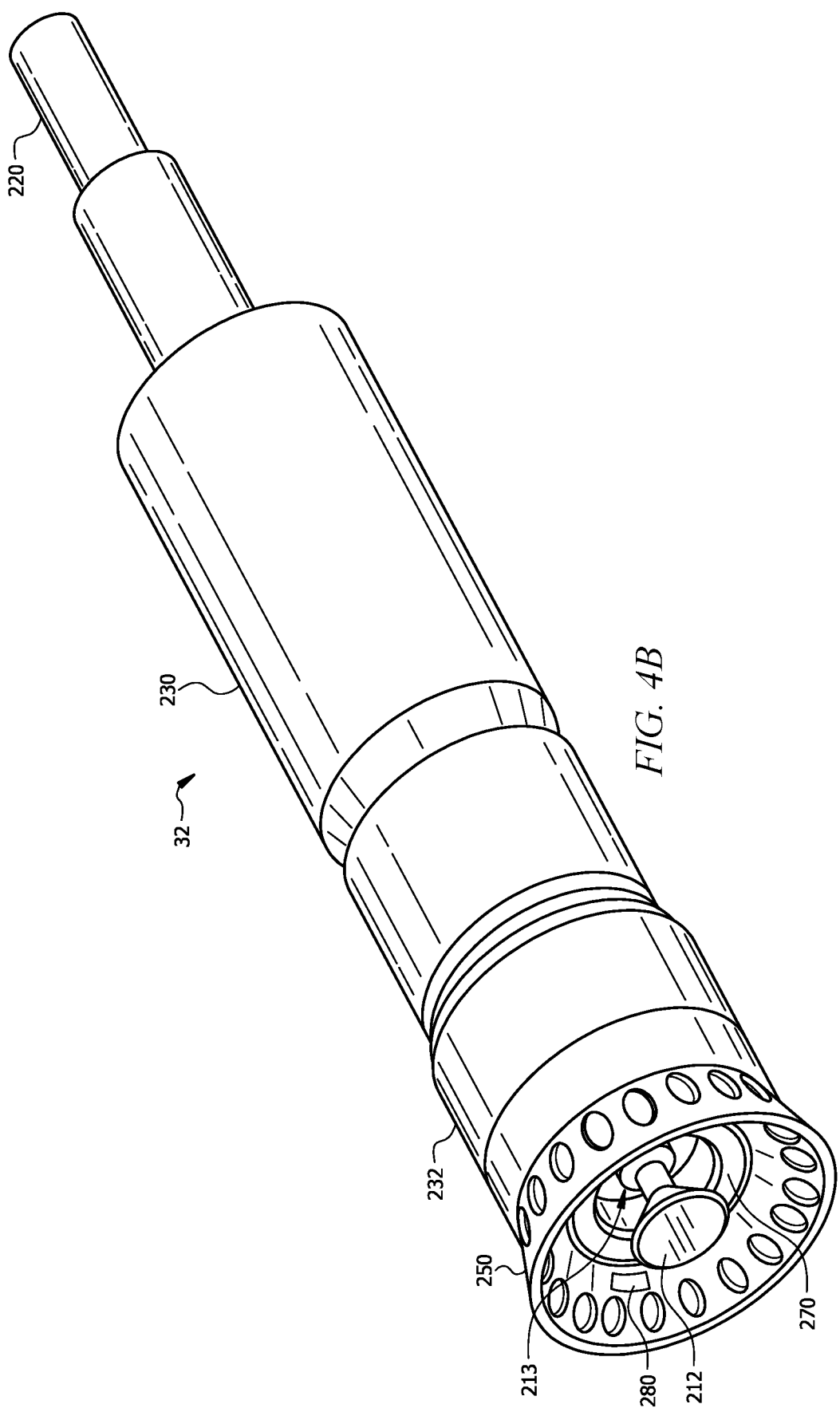
FIG. 4B is a perspective view of exemplary components of another bottom-hole assembly, in accordance with one or more embodiments of the present disclosure.

FIG. 4B is a perspective view of exemplary components of another bottom-hole assembly (e.g., BHA 32), in accordance with one or more embodiments of the present disclosure. BHA 32 may include discharge tool 230 and discharger 232. For the purposes of the present disclosure, discharger 232 may be integrated within the discharge tool 230 or may be a separate component that is coupled to discharge tool 230. BHA 32 and discharge tool 230 may include features and functionalities similar to those discussed above with reference to FIG. 4A.

Discharger 232 may include electrode 212, ground ring 250, and solid insulator 270. Electrode 212 may be placed approximately in the center of discharger 232. Electrode 212 may be positioned at a minimum distance from ground ring 250 of approximately 0.4 inches and at a maximum distance from ground ring 250 of approximately 6 inches. The distance between electrode 212 and ground ring 250 may be based on the parameters of the discharger operation and/or on the diameter of discharger 232. For example, the distance between electrode 212 and ground ring 250, at their closest spacing, may be at least 0.4 inches, at least 1 inch, at least 1.5 inches, or at least 2 inches. The distance between electrode 212 and ground ring 250 may be generally symmetrical or may be asymmetrical such that the electric field surrounding the drill bit has a symmetrical or asymmetrical shape. Electrode 212 may have any suitable diameter based on the discharger operation, the distance between electrode 212 and ground ring 250, and/or the diameter of discharger 232. For example, electrode 212 may have a diameter between approximately 2 and approximately 10 inches. Ground ring 250 may function as an electrode and provide a location on the discharger 232 where an electrical arc may initiate and/or terminate.

As described above with reference to FIGS. 1, 4A, and 4B, when the electric potential across electrodes (e.g., 208 and 210 and/or 250 and 212) of the discharger 232 becomes sufficiently large, an electrical discharge in the form of an electrical arc or spark may form through the rock formation 18 that is near the electrodes. The arc may include a substantially constant electrical discharge. The spark ma include a series of pulsed electric discharges. The arc or spark provides a temporary electrical short between the electrodes, and thus allows electric current to flow through the arc or spark inside a portion of the rock formation 18 proximate to the wellbore 16. The arc or spark increases the temperature of the portion of the rock formation through which the arc flows and the surrounding formation and materials. The temperature is sufficiently high to vaporize a portion of the rock formation 18 interacting with the arc or spark. The vaporization process creates a discharge plasma which emits light at wavelengths depending on the elemental composition of the portion of the rock that vaporized. As described in more detail below, the optical emission from the discharge plasma may be analyzed to determine the constituent elements and corresponding element concentrations in the rock formation.

In one or more embodiments, one or more of the electrodes, 208, 210, 250, 212 and 250 are designed to contact at least a portion of the rock formation 18 surrounding the discharge tool 230.

In operation, a sufficiently large difference in electrical potential between the electrodes of the discharger 232 produces an electrical discharge. This discharge passes through the portion of the rock formation 18 near the electrodes or in contact with one or more of the electrodes, heating and vaporizing the formation 18 at the surface and exciting the atoms of the formation 18. When the energy of an electrical discharge interacts with an atom of the formation 18, some of the electrons in the atom's outer shells are ejected. Outer-shell electrons are less tightly bound to the nucleus of the atom because they are further away from the nucleus and so require less input energy to be ejected. The ejected electrons create a vacancy making the atom unstable. To restore stability, electrons from higher orbits further away from the nucleus drop down to fill the vacancy. The excess energy released as the electrons move between the two energy levels or shells is emitted in the form of element-specific light or optical emission. Every element emits a series of spectral lines corresponding to the different electron transitions between the different energy levels or shells. Each transition produces a specific optical emission line with a fixed wavelength or energy of radiation. The optical emission including the multiple optical emission lines from the vaporized rock formation 18 may be referred to as discharge plasma. The excited atoms and ions in the discharge plasma create a unique emission spectrum specific to the constituent elements of the sample rock formation.

As shown in FIGS. 4A and 4B the discharge tool 230 may include one or more optically transparent windows 280 designed to pass at least a portion of the optical emission (e.g., including visible light) generated by the discharge plasma into an interior region (not shown) of the discharge tool 230. The optically transparent window 280 may be made of any transparent and durable material capable of withstanding downhole conditions. For example, the window 280 may be made of sapphire or aluminum oxynitride. The interior of the discharge tool 230 may house at least a portion of an OES sub-system. As described in more detail below, the OES sub-system may collect the optical emission passing through and received from the window 280, split the optical emission into element specific wavelengths, measure intensities of the light at different wavelengths and analyze data from the measurement to determine the elemental composition of the sample rock formation that was vaporized to generate the discharge plasma. The determined elemental composition of the sample rock formation may include one or more constituent elements of the sample and concentrations of each element in the sample. The term "element" refers to a fundamental chemical element or atomic element as shown in the periodic table.

FIG. 5 illustrates an OES subsystem 500, in accordance with one or more embodiments of the present disclosure. As shown, the OES subsystem 500 may include a collector 502, a monochromator 504, detectors 506 and an optical analyzer 508. As noted above, at least a portion of the OES subsystem may be housed inside the discharge tool 130, BHA 32 or a combination thereof. For example, at least the collector 502, monochromator 504 and detector 506 may be housed in the discharge tool 130, the BHA 32 or a combination there of. The optical analyzer 508 may be positioned in the discharge tool or the BHA, or at the surface. In one embodiment, the discharge tool 230 (including the discharger 232) and the OES sub-system may form an OES system. As shown in FIG. 5, the collector 502 is positioned in view of the window 280 and receives at least a portion of the optical emission 530 passing through the window 280 that includes light in the visible and non-visible electromagnetic spectrum. As described above, the optical emission 530 may be from a discharge plasma 520 generated as a result of vaporizing a sample rock formation using an electrical discharge. As described above, the sample rock formation is a portion of the rock formation 18 interacting with the electrical discharge produced by the electrodes of the discharger 232. The collector 502 collects the optical emission received through the window 280 and transmits the collected optical emission to the monochromator 504 via a first optical fiber line 510.

The optical emission 530 from the discharge plasma 520 may include a unique emission spectrum specific to the constituent elements of the sample rock formation. This emission spectrum may include emission spectral lines corresponding to each constituent element of the vaporized sample of the rock formation 18. A typical sample made of several constituent elements emits a line-rich spectrum, where each element emits light over several wavelengths. For example, iron emits just over 8000 different wavelengths. Further, the optical emission 530 may include noise from other emission in the non-visible electromagnetic spectrum. The part of the electromagnetic spectrum which is used by OES may include the visible spectrum and part of the ultraviolet spectrum. For example, in terms of wavelength, the usable spectrum includes wavelengths from 130 nanometers up to around 800 nanometers.

The monochromator 504 is responsible to select the optimum emission lines for a given element of the sample rock formation. The monochromator 504 separates the incoming light of the optical emission 530 (e.g., received from the collector 502 via the first optical fiber 510) into element-specific wavelengths. In one embodiment, the monochromator 504 may include a diffraction grating that extracts an emission spectrum relating to one or more constituent elements of the sample rock formation. In certain embodiments, the monochromator 504 may be configured to extract emission spectral lines corresponding to one or more desired elements. This may be useful when attempting to detect specific elements within a rock formation 18. The element-specific emission extracted by the monochromator 504 is then transmitted to the detector 506 via a second optical fiber 512.

Detector 506 may include a set of optical detectors that receive the extracted element-specific emission spectrums from the monochromator 504 via the second optical fiber 512 and measure an intensity of the emission spectrum relating to each corresponding one or more constituent elements. The intensity of light measured for an element is proportional to the concentration of the element in the sample. In one embodiment, each of the set of optical detectors of the detector 506 is designed to detect and measure the intensity of light for a particular element. In one embodiment, one or more of the detectors 506 includes a Charge Coupled Device (CCD) detector.

Optical analyzer 508 may be configured to receive the measured intensity of the detected emission spectrums relating to the one or more constituent elements of the sample rock formation and determine concentrations of each constituent element of the rock formation based on the measured intensity of the emission spectrum relating to the constituent element. The determined concentration of a constituent element is a function of the intensity of the emission corresponding to the element, wherein a higher intensity of the emission spectrum indicates a higher concentration of the respective constituent element. In one embodiment, the optical analyzer 508 may correspond to or implemented by any one of the data processing systems 45 and 50 shown in FIGS. 1 and 2 respectively. In one or more embodiments, the OES system can analyze a wide range of elements from Lithium to Uranium covering a wide concentration range, giving very high accuracy, high precision and low detection limits. The elements and concentrations that the optical analyzer 508 can determine depend on the sample rock being tested and the type of analyzer used.

In one or more embodiments, the discharge tool 230 is positioned on a portion of the drill string 8 uphole and away from the drill bit 14 positioned at a downhole end of the drill string 8. In fact, the discharge tool including the discharger 232 may be positioned anywhere along the length of the drill string 8 within the wellbore.

The downhole conditions are typically not fully known prior to a particular drilling operation and may change over the course of the operation. Because of these unknowns and the potential for changing conditions, one or more operating parameters of a drilling operation may be configured suboptimally when initializing the drilling operation and may become less optimally configured during a drilling operation due to changing conditions. In one or more embodiments, a controller of the system 100 may automatically determine that a modification should be made to one or more operating parameters of the drilling operation. The controller may also initiate the adjustment of one or more operating parameters to effect the desired modification by sending a command to a downhole tool (e.g., a tool of the BHA 32). In one embodiment, the controller may form a portion of the data processing system 50, wherein the data processing system 50 implements operations of the controller. For example, the controller may receive and analyze the elemental composition of the rock formation 18 reflecting changing conditions for the drilling operation or a change in drilling performance to determine whether to modify any of the current operating parameters of the drilling operation. More specifically, it may be determined that a drilling speed, drilling direction, hole caliper or hole quality, drilling process energy efficiency, taxing of the tool componentry, or other parameter indicative of the operational goals of the drilling operation and/or a type or property of mud, a BHA configuration (e.g., a position of a stabilizer or valve), a configuration of the drill bit 14 (e.g., a position or configuration of an insulator or nozzle), a controllable characteristic of the electrical circuits and/or other components of the discharge tool 230, and/or another operating parameter of the systems employed to meet the operational goals of the drilling operation should be modified to optimize the drilling operation in response to the determined elemental composition of the rock formation surrounding the wellbore during the drilling operation.

FIG. 6 illustrates example operations 600 for determining elemental composition of a rock formation, in accordance with certain aspects of the present disclosure.

At operation 602, a discharge tool 230 is positioned within a wellbore 16. In one or more embodiments, the discharge tool 230 may be mounted on the drill string 8 and lowered into the wellbore as the drill bit 14 cuts through the rock formation 18 creating the wellbore 16. As described above with reference to FIGS. 4A and 4B, the discharge tool 230 may be part of or included in the BHA 32. Alternatively, the discharge tool 230 may be positioned (e.g., mounted) on a portion of the drill string 8 uphole and away from a drill bit 14. The position of the discharge tool 230 within the wellbore may be decided based on the portion of the rock formation 18 to be analyzed for elemental composition.

At operation 604, an electrical discharge is generated using the discharge tool 230. The electrical discharge interacts with the rock formation 18 proximate to the discharge tool 230, wherein the interaction of the electrical discharge with the rock formation 18 vaporizes a portion of the rock formation 18 to generate a discharge plasma. As described above, discharge tool 230 may provide pulsed electrical energy to discharger 232. Discharge tool 230 receives electrical power from a power source via cable 220. For example, discharge tool 230 may receive electrical power via cable 220 from a power source located on the surface or from a power source located downhole such as a generator powered by a mud turbine. Discharge tool 230 may also receive electrical power via a combination of a power source located on the surface and a power source located downhole. Discharger 232 may include one or more electrodes 208 and 210 and a ground ring 250, shown in part in FIG. 4A. Ground ring 250 may function as an electrode. Discharge tool 230 converts electrical power received from the power source into high-energy electrical pulses that are applied across electrodes 208 and/or 210 and ground ring 250 of the discharger 232.

When the electric potential across electrodes (e.g., 208 and 210 and/or 250 and 212) of the discharger 232 becomes sufficiently large, an electrical discharge in the form of an electrical arc or spark may form through the rock formation 18 that is near the electrodes. The arc may include a substantially constant electrical discharge. The spark may include a series of pulsed electric discharges. The arc or spark provides a temporary electrical short between the electrodes, and thus allows electric current to flow through the arc or spark inside a portion of the rock formation 18 proximate to the wellbore 16. The arc or spark increases the temperature of the portion of the rock formation through which the arc flows and the surrounding formation and materials. The temperature is sufficiently high to vaporize a portion of the rock formation 18 interacting with the arc or spark. The vaporization process creates a discharge plasma which emits light at wavelengths depending on the elemental composition of the portion of the rock that vaporized. The optical emission from the discharge plasma may be analyzed to determine the constituent elements and corresponding element concentrations in the rock formation.

At operation 606, using an optical emission spectroscopy (OES) sub-system, an elemental composition of the portion of the rock formation (e.g., sample rock formation) is determined based on optical emission generated by the discharge plasma, wherein at least a portion of the OES sub-system is positioned within the wellbore.

As described above with reference to FIG. 5, the OES subsystem 500 may include a collector 502, a monochromator 504, detectors 506 and an optical analyzer 508. As noted above, at least a portion of the OES sub-system may be housed inside the discharge tool 130, BHA 32 or a combination thereof. For example, at least the collector 502, monochromator 504 and detector 506 may be housed in the discharge tool 130, the BHA 32 or a combination there of. The optical analyzer 508 may be positioned in the discharge tool or the BHA, or at the surface. In one embodiment, the discharge tool 230 (including the discharger 232) and the OES sub-system may form an OES system. As shown in FIG. 5, the collector 502 is positioned in view of the window 280 and receives at least a portion of the optical emission 530 passing through the window 280 that includes light in the visible and non-visible electromagnetic spectrum. As described above, the optical emission 530 may be from a discharge plasma 520 generated as a result of vaporizing a sample rock formation using an electrical discharge. As described above, the sample rock formation is a portion of the rock formation 18 interacting with the electrical discharge produced by the electrodes of the discharger 232. The collector 502 collects the optical emission received through the window 280 and transmits the collected optical emission to the monochromator 504 via a first optical fiber line 510.

The optical emission 530 from the discharge plasma 520 may include a unique emission spectrum specific to the constituent elements of the sample rock formation. This emission spectrum may include emission spectral lines corresponding to each constituent element of the vaporized sample of the rock formation 18. A typical sample made of several constituent elements emits a line-rich spectrum, where each element emits light over several wavelengths.

The monochromator 504 is responsible to select the optimum emission lines for a given element of the sample rock formation. The monochromator 504 separates the incoming light of the optical emission 530 (e.g., received from the collector 502 via the first optical fiber 510) into element-specific wavelengths. In one embodiment, the monochromator 504 may include a diffraction grating that extracts an emission spectrum relating to one or more constituent elements of the sample rock formation. In certain embodiments, the monochromator 504 may be configured to extract emission spectral lines corresponding to one or more desired elements. This may be useful when attempting to detect specific elements within a rock formation 18. The element-specific emission extracted by the monochromator 504 is then transmitted to the detector 506 via a second optical fiber 512.

Detector 506 may include a set of optical detectors that receive the extracted element-specific emission spectrums from the monochromator 504 via the second optical fiber 512 and measure an intensity of the emission spectrum relating to each corresponding one or more constituent elements. The intensity of light measured for an element is proportional to the concentration of the element in the sample. In one embodiment, each of the set of optical detectors of the detector 506 is designed to detect and measure the intensity of light for a particular element. In one embodiment, one or more of the detectors 506 includes a Charge Coupled Device (CCD) detector.

Optical analyzer 508 may be configured to receive the measured intensity of the detected emission spectrums relating to the one or more constituent elements of the sample rock formation and determine concentrations of each constituent element of the rock formation based on the measured intensity of the emission spectrum relating to the constituent element. The determined concentration of a constituent element is a function of the intensity of the emission corresponding to the element, wherein a higher intensity of the emission spectrum indicates a higher concentration of the respective constituent element. In one embodiment, the optical analyzer 508 may correspond to or implemented by any one of the data processing systems 45 and 50 shown in FIGS. 1 and 2 respectively. In one or more embodiments, the OES system can analyze a wide range of elements from Lithium to Uranium covering a wide concentration range, giving very high accuracy, high precision and low detection limits. The elements and concentrations that the optical analyzer 508 can determine depend on the sample rock being tested and the type of analyzer used.

In one or more embodiments, the discharge tool 230 is positioned on a portion of the drill string 8 uphole and away from the drill bit 14 positioned at a downhole end of the drill string 8. In fact, the discharge tool including the discharger 232 may be positioned anywhere along the length of the drill string 8 within the wellbore.

Therefore, the present disclosure is well adapted to attain the ends and advantages mentioned as well as those that are inherent therein. The particular aspects disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative aspects disclosed above may be altered or modified and all such variations are considered within the scope and spirit of the present disclosure. Also, the terms in the claims have their plain, ordinary meaning unless otherwise explicitly and clearly defined by the patentee. The indefinite articles "a" or "an," as used in the claims, are defined herein to mean one or more than one of the elements that it introduces.

Embodiments of the present disclosure provide a system comprising a discharge tool positioned within a wellbore and configured to generate an electrical discharge that interacts with a rock formation proximate to the discharge tool, wherein the interaction of the electrical discharge with the rock formation vaporizes a portion of the rock formation to generate a discharge plasma; and an optical emission spectroscopy (OES) sub-system configured to determine an elemental composition of the portion of the rock formation based on optical emission generated by the discharge plasma, wherein at least a portion of the OES sub-system is positioned within the wellbore.

In one embodiment, the discharge tool further comprises an optically transparent window positioned in view of the discharge plasma, wherein at least a portion of the optical emission generated by the discharge plasma passes through the optically transparent window.

In one embodiment, the OES sub-system comprises a collector positioned in view of the optically transparent window, wherein the collector receives the portion of the optical emission passing through the optically transparent window, collects the received optical emission and transmits the collected optical emission via a first optical fiber; a monochromator that receives the optical emission from the collector via the first optical fiber and extracts an emission spectrum relating to each of one or more constituent chemical elements of the rock formation; a set of optical detectors that receive the extracted emission spectrums from the monochromator via a second optical fiber and measure an intensity of the emission spectrum relating to each of the one or more constituent chemical elements; and an optical analyzer configured to: receive the measured intensity of the detected emission spectrums relating to the one or more constituent chemical elements; and determine concentration of each constituent chemical element of the rock formation based on the measured intensity of the emission spectrum relating to the constituent chemical element, wherein a higher intensity of the emission spectrum indicates a higher concentration of the respective constituent chemical element.

In one embodiment, the monochromator is designed to extract the emission spectrum of a pre-selected set of chemical elements.

In one embodiment, each of the set of optical detectors detects the emission spectrum relating to a different chemical element.

In one embodiment, the set of optical detectors comprises one or more Charge Coupled Device (CCD) detectors.

In one embodiment, the discharge tool comprises at least one electrode that generates the electrical discharge, wherein the at least one electrode is in physical contact with the rock formation.

In one embodiment, the electrical discharge comprises at least one of a substantially constant arc or a spark including a series of pulsed electrical discharges.

In one embodiment, the OES sub-system is part of the discharge tool.

In one embodiment, the elemental composition of the rock formation comprises constituent chemical elements of the rock formation, wherein each of the constituent chemical elements is a fundamental chemical element of the periodic table.

In one embodiment, the discharge tool is positioned on a portion of a drill string uphole and away from a drill bit positioned at a downhole end of the drill string used to drill the wellbore.

Embodiments of the present disclosure provide a method for determining elemental composition of a rock formation, comprising: positioning a discharge tool within a wellbore; generating using the discharge tool, an electrical discharge that interacts with the rock formation proximate to the discharge tool, wherein the interaction of the electrical discharge with the rock formation vaporizes a portion of the rock formation to generate a discharge plasma; and determining using an optical emission spectroscopy (OES) sub-system, an elemental composition of the portion of the rock formation based on optical emission generated by the discharge plasma, wherein at least a portion of the OES sub-system is positioned within the wellbore.

In one embodiment, generating the electrical discharge comprises: passing least a portion of the optical emission generated by the discharge plasma through an optically transparent window of the discharge tool that is positioned in view of the discharge plasma.

In one embodiment, generating the electrical discharge further comprises: collecting the portion of the optical emission passing through the optically transparent window using a collector of the OES sub-system positioned in view of the optically transparent window; extracting from the collected optical emission, an emission spectrum relating to each of one or more constituent chemical elements of the rock formation using a monochromator of the OES sub-system; measuring an intensity of the emission spectrum relating to each of the one or more constituent chemical elements using a set of optical detectors of the OES sub-system; and using an optical analyzer of the OES sub-system to: receive the measured intensity of the detected emission spectrums relating to the one or more constituent chemical elements; and determine concentration of each constituent chemical element of the rock formation based on the measured intensity of the emission spectrum relating to the constituent chemical element, wherein a higher intensity of the emission spectrum indicates a higher concentration of the respective constituent chemical element.

In one embodiment, the monochromator is designed to extract the emission spectrum of a pre-selected set of chemical elements.

In one embodiment, each of the set of optical detectors detects the emission spectrum relating to a different chemical element.

In one embodiment, the set of optical detectors comprises one or more Charge Coupled Device (CCD) detectors.

In one embodiment, the method further comprises generating the electrical discharge using at least one electrode of the discharge tool, wherein the at least one electrode is in physical contact with the rock formation.

In one embodiment, the electrical discharge comprises at least one of a substantially constant arc or a spark including a series of pulsed electrical discharges.

In one embodiment, the OES sub-system is part of the discharge tool.

What is claimed is:

1. A system comprising:
   a discharge tool positioned within a wellbore and configured to generate an electrical discharge that interacts with a rock formation proximate to the discharge tool, wherein the interaction of the electrical discharge with the rock formation vaporizes a portion of the rock formation to generate a discharge plasma, and wherein the discharge tool comprises an optically transparent window positioned in view of the discharge plasma, wherein at least a portion of optical emission generated by the discharge plasma passes through the optically transparent window; and
   an optical emission spectroscopy (OES) sub-system configured to determine an elemental composition of the portion of the rock formation based on the optical emission generated by the discharge plasma, wherein at least a portion of the OES sub-system is positioned within the wellbore.

2. The system of claim 1, wherein the OES sub-system comprises:
   a collector positioned in view of the optically transparent window, wherein the collector receives the portion of the optical emission passing through the optically transparent window, collects the received optical emission and transmits the collected optical emission via a first optical fiber;
   a monochromator that receives the optical emission from the collector via the first optical fiber and extracts an emission spectrum relating to each of one or more constituent chemical elements of the rock formation;
   a set of optical detectors that receive the extracted emission spectrums from the monochromator via a second optical fiber and measure an intensity of the emission spectrum relating to each of the one or more constituent chemical elements; and
   an optical analyzer configured to:
      receive the measured intensity of the detected emission spectrums relating to the one or more constituent chemical elements; and
      determine concentration of each constituent chemical element of the rock formation based on the measured intensity of the emission spectrum relating to the constituent chemical element, wherein a higher intensity of the emission spectrum indicates a higher concentration of the respective constituent chemical element.

3. The system of claim 2, wherein the monochromator is designed to extract the emission spectrum of a pre-selected set of chemical elements.

4. The system of claim 2, wherein each optical detector of the set of optical detectors detects the emission spectrum relating to a different chemical element.

5. The system of claim 2, wherein the set of optical detectors comprises one or more Charge Coupled Device (CCD) detectors.

6. The system of claim 1, wherein the discharge tool comprises:
   at least one electrode that generates the electrical discharge, wherein the at least one electrode is in physical contact with the rock formation.

7. The system of claim 1, wherein the electrical discharge comprises at least one of a substantially constant arc or a spark including a series of pulsed electrical discharges.

8. The system of claim 1, wherein the OES sub-system is part of the discharge tool.

9. The system of claim 1, wherein the elemental composition of the rock formation comprises constituent chemical elements of the rock formation, wherein each of the constituent chemical elements is a fundamental chemical element of the periodic table.

10. The system of claim 1, wherein the discharge tool is positioned on a portion of a drill string uphole and away from a drill bit positioned at a downhole end of the drill string used to drill the wellbore.

11. A method for determining elemental composition of a rock formation, comprising:

positioning a discharge tool within a wellbore;

generating, using the discharge tool, an electrical discharge that interacts with the rock formation proximate to the discharge tool, wherein the interaction of the electrical discharge with the rock formation vaporizes a portion of the rock formation to generate a discharge plasma, and wherein generating the electrical discharge comprises passing least a portion of optical emission generated by the discharge plasma through an optically transparent window of the discharge tool that is positioned in view of the discharge plasma; and determining, using an optical emission spectroscopy (OES) sub-system, an elemental composition of the portion of the rock formation based on the optical emission generated by the discharge plasma, wherein at least a portion of the OES sub-system is positioned within the wellbore.

12. The method of claim 11, wherein generating the electrical discharge further comprises:

collecting the portion of the optical emission passing through the optically transparent window using a collector of the OES sub-system positioned in view of the optically transparent window;

extracting from the collected optical emission, an emission spectrum relating to each of one or more constituent chemical elements of the rock formation using a monochromator of the OES sub-system;

measuring an intensity of the emission spectrum relating to each of the one or more constituent chemical elements using a set of optical detectors of the OES sub-system; and using an optical analyzer of the OES sub-system to:

receive the measured intensity of the detected emission spectrums relating to the one or more constituent chemical elements; and determine concentration of each constituent chemical element of the rock formation based on the measured intensity of the emission spectrum relating to the constituent chemical element, wherein a higher intensity of the emission spectrum indicates a higher concentration of the respective constituent chemical element.

13. The method of claim 12, wherein the monochromator is designed to extract the emission spectrum of a pre-selected set of chemical elements.

14. The method of claim 12, wherein each optical detector of the set of optical detectors detects the emission spectrum relating to a different chemical element.

15. The method of claim 12, wherein the set of optical detectors comprises one or more Charge Coupled Device (CCD) detectors.

16. The method of claim 11, further comprising:

generating the electrical discharge using at least one electrode of the discharge tool, wherein the at least one electrode is in physical contact with the rock formation.

17. The method of claim 11, wherein the electrical discharge comprises at least one of a substantially constant arc or a spark including a series of pulsed electrical discharges.

18. The method of claim 11, wherein the OES sub-system is part of the discharge tool.

* * * * *